United States Patent [19]
Moffett

[11] Patent Number: 4,462,256
[45] Date of Patent: Jul. 31, 1984

[54] LIGHTWEIGHT, BROADBAND RAYLEIGH WAVE TRANSDUCER

[75] Inventor: Mark B. Moffett, Waterford, Conn.

[73] Assignee: The United States of America as represented by the Secretary of the Navy, Washington, D.C.

[21] Appl. No.: 453,631

[22] Filed: Dec. 27, 1982

[51] Int. Cl.³ ............................................. G01N 29/04
[52] U.S. Cl. .................... 73/642; 310/313 R
[58] Field of Search ................. 73/642, 644, 629, 617; 310/313 A, 313 R

[56] References Cited

U.S. PATENT DOCUMENTS 2,912,854 11/1959 Schubring ............................. 73/644
3,534,300 10/1970 Jouffroy et al. .................... 310/313
4,011,747 3/1977 Shaw ..................................... 73/642

Primary Examiner—Anthony V. Ciarlante
Attorney, Agent, or Firm—Robert F. Beers; Arthur A. McGill; Michael J. McGowan

[57] ABSTRACT

A broadband angle-beam transducer system for producing and/or receiving Rayleigh waves on the surface of a metal medium comprising a thickness mode piezoelectric polymer transducer element embedded within and impedance matched to a plastic wedge. The transducer element is oriented at an angle determined to be the critical angle for Rayleigh waves in the metal structure to be tested. As a transmitter, the transducer element generates discrete dilatational wave pulses, one of which propagates within the plastic wedge to the plastic face in contact with the metal structure. At this face some of the wave energy is reflected as dilatational and shear waves within the wedge and the remainder of the wave energy passes through a coupling medium into the metal structure producing a Rayleigh wave traveling along the surface of the structure. When the system is used as a receiver, a Rayleigh wave propagating on the surface of the metal structure is received by the polymer element which then generates a voltage proportional to the Rayleigh waveform.

30 Claims, 4 Drawing Figures

LIGHTWEIGHT, BROADBAND RAYLEIGH WAVE TRANSDUCER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates to transducer devices and more particularly to a broadband, lightweight Rayleigh wave transducer suitable for structural calibration, locating structural emission sources and detecting near-surface flaws using pulse-echo techniques.

2. Description of the Prior Art

Acoustic emission structural calibration is commonly performed either with a narrowband piezoelectric source or with a broadband mechanical source, such as the breaking of a glass capillary tube or a pencil lead. Narrowband sources however do not permit good pulse arrival time resolution. Broadband mechanical sources are very inconvenient to use because triggering is difficult to set up, the pulse shape and amplitude are not repeatable, the pulse repetition rate is very low and a transient-capture device is required to record the waveform. A piezoelectric thickness vibrator can be made broadband if an appropriate damping material is applied to one of the vibrator faces. However the search for an effective damping material is usually a time-consuming, cut-and-try process.

Acoustic emission technology usually involves the generation and reception of Rayleigh wave pulses on a solid surface. Rayleigh waves can be produced and detected by transducers whose motion is normal to the surface, but this method requires that the lateral dimensions be smaller than the Rayleigh wavelength. This is a severe restriction at high frequencies, i.e., $>1$ MHz, resulting in low capacitance and sensitivity. Rayleigh waves can be effectively generated or received over larger areas by interdigital transducers and by angle-beam transducers. Interdigital transducers are extensively used in surface-acoustic-wave devices but are inherently narrowband, because the interdigital spacing is fixed at one-half the wavelength at the frequency of interest. Present angle-beam transducers utilize a thickness-mode transducer element coupled to a plastic wedge inclined at the critical angle for Rayleigh waves in the material to be examined. Such angle-beam transducers however are normally narrowband devices due to impedance mismatches between the element and the plastic wedge.

SUMMARY OF THE INVENTION

Accordingly, it is a general purpose and object of the present invention to provide an electrical means of producing and receiving broadband, short pulse Rayleigh waves on the surface of a solid metal structure for determining transmission characteristics of the structure. Another object is to detect surface flaws in a metal structure using pulse-echo techniques. A further object is that such electrical means be lightweight and rugged. Still another object is that such device use a thickness-mode piezoelectric polymer transducer element embedded within a plastic wedge. A still further object is that the impedance of the transducer element be closely matched to the characteristic impedance of the plastic wedge. These and other objects of the present invention will become apparent when considered in conjunction with the specification and drawings.

These objects are accomplished with the present invention by providing a broadband angle-beam transducer device comprising a thickness-mode piezoelectric polymer transducer element embedded within and impedance matched to a plastic wedge. The transducer element is inclined at an angle which is the critical angle for Rayleigh waves in the metal structure to be examined. A voltage waveform generator attached to the transducer element causes strain pulses to propagate in directions normal to the element faces. Dilatational waves traveling in the direction of the test item upon reaching the transducer surface, split into shear, dilatational and Rayleigh waves. Only the Rayleigh waves pass through the coupling medium and into the metal structure subsequently propagating along the surface thereof. Remaining shear and dilatational waves are delayed by propagating within the plastic wedge for a preselected period to allow time separation from the initial Rayleigh pulse. Operating as a receiver a Rayleigh wave in the material is received by the piezoelectric polymer transducer element which then generates a voltage proportional to the Rayleigh waveform. The device thus provides an electrical means of producing and receiving broadband, short pulse Rayleigh waves traveling on the surfaces of solid metal structures which may then be used for determining material transmission characteristics, i.e., structural calibration, locating acoustic emission sources within a structure and detecting near-surface flaws using pulse-echo techniques.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
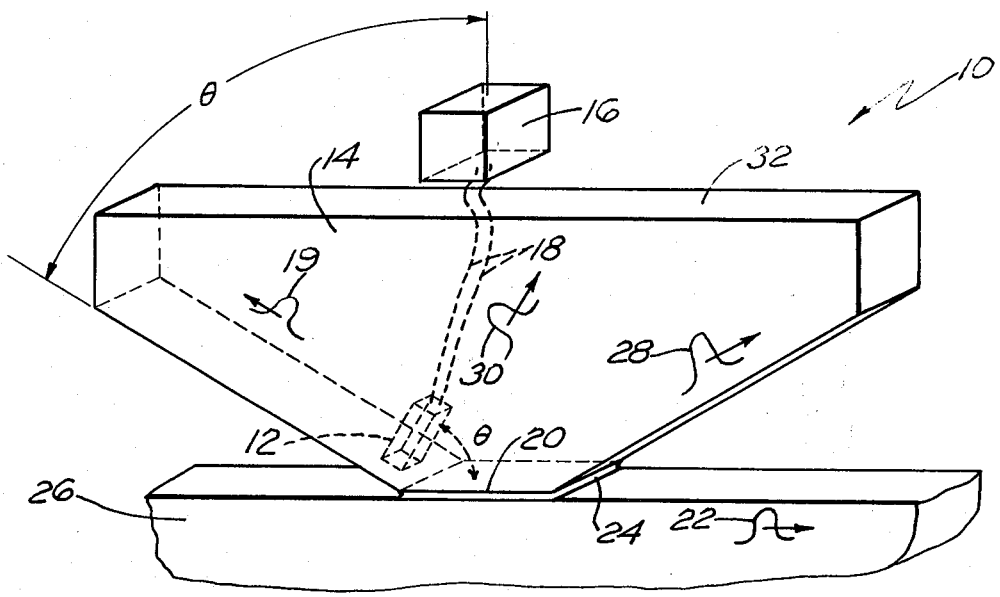
FIG. 1 shows a broadband Rayleigh wave transducer built according to the teachings of subject invention.

In any solid medium, strain pulses propagate as dilatational, shear and Rayleigh waves. A dilatational wave is a longitudinal Pressure wave propagating within the solid. A shear wave exhibits motion transverse to its direction of propagation within the solid. A Rayleigh wave has both longitudinal and transverse components to its motion which may best be described as elliptical like that of an ocean wave. Rayleigh waves are elastic perturbations propagating near the free boundary of a solid and decaying with depth.

A dilatational wave traveling within a solid and impinging on a surface of the solid in contact with a second solid at an incident angle $\theta$ with respect to an axis normal to the surface and moving at a longitudinal velocity $v_l$ will divide into reflected dilatational and shear waves, and a refracted wave passing into the second solid at velocity $v_2$ at an angle $\theta_2$ with respect to the normal. Snell's law establishes the relationship of the incident wave to the refracted wave as $v_1/\sin \theta = v_2/\sin \theta_2$. Rearranging factors yields: $\sin \theta_2 = (v_2/v_1)\sin \theta$. For a given angle $\theta$, $\theta_2$ will depend on the ratio of $v_2$ to $v_1$ where both velocities are dependent upon material properties of the two solids and the wave type. It should be noted that in a typical solid, the shear wave velocity is approximately $\frac{3}{5}$ the velocity of the dilatational wave and the Rayleigh wave velocity is approximately 9/10 the velocity of the shear wave. If the velocities of the dilatational and shear waves in the second solid are larger than $v_1$, and if $\sin \theta$ is greater than $v_1/v_2$, for both waves, then they will be totally reflected at the interface between the solids. By increasing $\theta$ still further until $\sin \theta = v_1/v_R$, where $v_R$ is the Rayleigh wave speed in the second medium, the only refracted waves will be Rayleigh waves which will propagate along the surface of the second solid. Since $v_1$ must be less than $v_R$, and since the second solid is typically a metal, the incident medium must be a relatively slow-velocity material, e.g., polystyrene or polymethyl methacrylate (PMMA).

The instant invention is an angle-beam transducer which is made broadband by the introduction of a thickness-mode piezoelectric polymer transducer element such as polyvinylidene fluoride (PVF$_2$). A thickness-mode element vibrates in the direction of the thin dimension. Unlike piezoelectric ceramic materials, polymers such as PVF$_2$ can be impedance-matched to a plastic wedge where the characteristic impedance of a material is defined as the material density times the dilatational wave speed. For example, the characteristic impedance of PVF$_2$ is about $4.1 \times 10^6$ mks Rayls which would closely match a plastic wedge of PMMA having an impedance of $3.5 \times 10^6$ mks Rayls. An even closer match can be achieved using materials such as filled epoxies. Impedance matching prevents ringing in the transducer element thus allowing reproduction of any single pulse signal given to it, thereby giving the device a broadband capability.

Referring now to FIG. 1 there is shown a Rayleigh wave transducer 10 comprising a PVF$_2$ thickness-mode transducer element 12 embedded at preselected angle $\theta$ within and impedance matched to a planar plastic wedge 14. When a suitable voltage waveform, e.g., a step, from generator 16 is applied to element 12 via electrical leads 18, strain pulses of duration $h/v^D$ propagate in opposite directions normal to PVF$_2$ element 12, one of which is dilatational pulse 19. As used herein $v^D$ is the open circuit dilatational wave speed in PVF$_2$ and h is the thickness of the PVF$_2$ element. Element 12 is made large enough in area to insure collimation at the frequency band of interest. At the plastic surface of transducer face 20 a Rayleigh pulse is transmitted via coupling medium 24 into and along the surface of metal structure 26. Medium 24 may be either a viscous liquid or a rigid bond material. The angle $\theta$ is the critical angle for generation of Rayleigh waves as determined using Snell's law. No dilatational or shear waves are transmitted into metal structure 26 since their wave speeds are greater than the Rayleigh wave velocity and $\theta$ is therefore greater than the critical angle for their generation. Dilatational and shear pulses 28 and 30 respectively, have been reflected from transducer face 20 and eventually, after reflection from upper transducer surface 32, will return to transducer face 20 and be partially transmitted into metal structure 26. Therefore plastic wedge 14 is made sufficiently large that these later transmissions occur outside the time window of interest.

Figure 2:
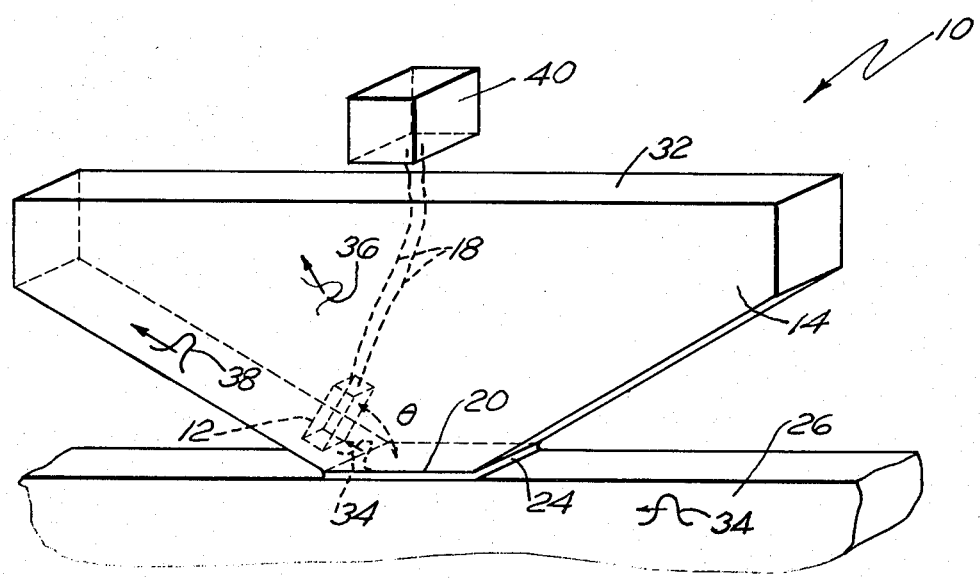
FIG. 2 shows the Rayleigh wave transducer taught in FIG. 1, used as a Rayleigh wave sensor.

The operation of the device as a Rayleigh-wave sensor is depicted in FIG. 2. Here an incoming Rayleigh pulse 34 in metal structure 26 produces shear and dilatational pulses 36 and 38, respectively, in planar plastic wedge material 14. Because of the close impedance match between PVF$_2$ transducer element 12 and plastic material 14, pulses 36 and 38 are not reflected from PVF$_2$ element 12 but are transmitted through it without appreciable attenuation. However, only the dilatational pulses 38 are sensed by PVF$_2$ element 12 since the element's response is highly directional and the output voltage, which is porportional to the dilatational pulse 38 and Rayleigh pulse 34 waveforms, is fed to preamplifier 40 via electrical leads 18.

The invention provides broadband short Rayleigh pulses, rather than the narrowband, oscillatory pulses normally generated by piezoelectric sources. As a Rayleigh pulse receiver, it has a flat, broadband response rather than the resonant response typical of narrowband piezoelectric sensors. The design of the device is straightforward since it requires only knowledge of characteristic impedances, rather than damping factors, of candidate materials. Pulses are repeatable in waveform and in amplitude. The repetition rate can be quite high and transient-capture capabilities are not required for the display system. Because the transducer is constructed largely of plastic materials in view of their slower propagation speeds, it is lighter in weight and smaller in size than piezoceramic-metal transducers. Unlike conventional acoustic emission transducers whose motion is all in phase, transducer face 20 is phased to receive Rayleigh waves and does not have to be small compared to a Rayleigh wavelength in order to have a smooth response at high frequencies. Because the transducer face 20 is a plastic material it serves as a wear plate, i.e., the transducer is more rugged than designs which call for the sensing element to be part of the transducer face. Since the couplant medium between transducer face 20 and metal structure 26 can be liquid, the transducer can be easily moved from one location to another on the solid surface of the structure if desired.

What has thus been described is a broadband angle-beam transducer device comprising a thickness-mode piezoelectric polymer transducer element embedded within and impedance matched to a plastic wedge. The element is inclined at an angle which is the critical angle for Rayleigh waves in the material to be examined. A voltage waveform generator attached to the transducer element causes strain pulses to propagate in directions normal to the element faces. The dilatational waves traveling in the direction of the test item upon reaching the transducer surface split into shear, dilatational and Rayleigh waves of which only the Rayleigh waves pass through the coupling medium and into the material subsequently propagating along the surface thereof. The reflected shear and dilatational waves are delayed by propagating within the plastic wedge for a preselected interval to allow time separation from the initial Rayleigh pulse. Operating as a receiver, a Rayleigh wave in the material is received by the piezoelectric polymer transducer element which generates a voltage proportional to the Rayleigh waveform. The device thus provides an electrical means of producing and receiving broadband, short pulse Rayleigh waves on the surface of solid structures for determining material transmission characteristics, i.e., structural calibration, locating acoustic emission sources within a structure and detecting near-surface flaws using pulse-echo techniques.

Figure 3:
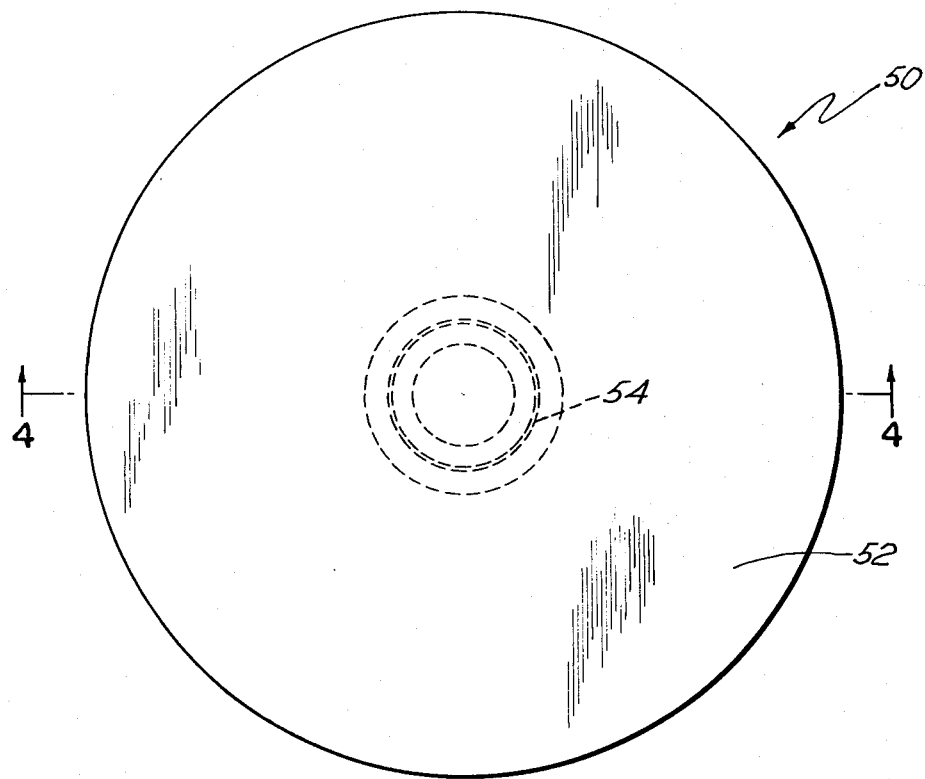
FIG. 3 shows a circularly symmetric omnidirectional configuration Rayleigh wave transducer.
Figure 4:
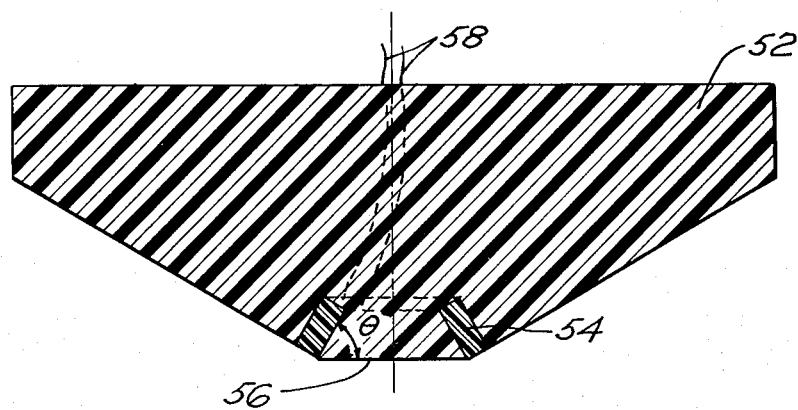
FIG. 4 is a sectional view of the device of FIG. 3 taken along line 4—4 thereof.

Obviously many modifications and variations of the present invention may become apparent in light of the above teachings: For example, as described above, the planar plastic wedge transducer is a directional device, with the directivity depending on the dimensions of the transducer face. The transducer can be made omnidirectional, however, by giving it circular symmetry. As shown in FIG. 3, transducer 50 comprises conical plastic wedge 52 having embedded therein piezoelectric polymer conical element 54. The sectional view, FIG. 4, shows additional details of the conical transducer configuration. Plastic wedge 52 is shown to have the same cross-sectional shape as a planar transducer. Polymer element 54 is inclined at the critical Rayleigh angle $\theta$ with respect to a normal through face 56. Conductors 58 connect through plastic wedge 52 to a chosen source. Alternatively a quasi-conical surface could be constructed from a plurality of plane segments to approximate a conical shape. Piezoelectric polymer materials other than $PVF_2$ can be used for the thickness-mode transducer element as long as a suitable plastic material matching the piezoelectric polymer impedance is selected.

When used as a sensor, it is usually convenient to mount the preamplifier directly on the upper surface of the transducer but the preamplifier may be situated at any other desired location.

As described above, the transducer is not suitable for continuous-wave operation because multiple reflections within the plastic material limit the useful time window. In other words, the size of the device determines its low-frequency response. To increase the time window and extend the response downward in frequency, the upper face may be coated with a suitable damping material to reduce the reflected wave amplitudes. Absorption within the plastic material will also provide some damping of these reflections, but the absorption properties of material must be low enough to permit nondispersive transmission between the thickness-mode transducer element and the transducer face.

In light of the above, it is therefore understood that within the scope of the appended claims, the invention may be practiced otherwise than as specifically described.

What is claimed is:

1. An angle-beam transducer for producing Rayleigh waves in a metal structure, comprising:
    a pulse generator adapted to produce a voltage pulse;
    a plurality of conductors, attached to said pulse generator, for receiving and transmitting said voltage pulse from said pulse generator;
    piezoelectric polymer transducer means, attached to said plurality of conductors, for receiving said voltage pulse from said plurality of conductors and converting said voltage pulse to a proportional strain pulse;
    wedge means, surrounding and embedding said plurality of conductors and said piezoelectric polymer transducer means such that said transducer means is oriented within said wedge means at the critical angle for generating Rayleigh waves in the metal structure being tested, said wedge means being impedance matched to said transducer means thereby allowing broadband pulse generation and such that said strain pulse has a smaller dilatation wave velocity in said wedge means than the Rayleigh wave velocity in the metal structure under test; and
    a couplant medium located between the face of said wedge means and the surface of said metal structure, for enhancing transmission of the refracted portion of said strain pulse into and along the surface of said metal structure.

2. An angle-beam transducer according to claim 1 wherein said plurality of conductors further comprise wires.

3. An angle-beam transducer according to claim 2 wherein said transducer means further comprises a thickness-mode piezoelectric polymer element.

4. An angle-beam transducer according to claim 3 wherein said wedge means is a plastic material having an impedance generally the same as said piezoelectric polymer element.

5. An angle-beam transducer according to claim 4 wherein said piezoelectric polymer is a polyvinylidene flouride.

6. An angle-beam transducer according to claim 5 wherein said plastic material is a polymethyl methacrylate.

7. An angle-beam transducer according to claim 6 wherein said wedge means further comprises a directional planar wedge having a preselected thickness and said polymer element further comprises a rectangular shaped element having a width corresponding to said wedge thickness.

8. An angle-beam transducer according to claim 6 wherein said wedge means further comprises a conical wedge having a preselected radius and said polymer element further comprises a corresponding conical element shaped such that an omnidirectional transducer is formed thereby.

9. An angle beam transducer according to claim 5 wherein said plastic material is a polystyrene.

10. An angle-beam transducer according to claim 9 wherein said wedge means further comprises a directional planar wedge having a preselected thickness and said polymer element further comprises a rectangular shaped element having a width corresponding to said wedge thickness.

11. An angle-beam transducer according to claim 9 wherein said wedge means further comprises a conical wedge having a preselected radius and said polymer element further comprises a corresponding conical element shaped such that an omnidirectional transducer is formed thereby.

12. An angle-beam transducer according to claim 3 wherein said wedge means is a filled epoxy having an impedance generally the same as said piezoelectric polymer element.

13. An angle-beam transducer according to claim 12 wherein said piezoelectric polymer is a polyvinylidene flouride.

14. An angle-beam transducer according to claim 13 wherein said wedge means further comprises a directional planar wedge having a preselected thickness and said polymer element further comprises a rectangular shaped element having a width corresponding to said wedge thickness.

15. An angle-beam transducer according to claim 13 wherein said wedge means further comprises a conical wedge having a preselected radius and said polymer element further comprises a corresponding conical element shaped such that an omnidirectional transducer is formed thereby.

16. An angle-beam transducer for sensing Rayleigh waves propagating along the surface of a metal structure, comprising:
   wedge means, having the face thereof in contact with said surface for receiving said Rayleigh wave from said metal structure;
   a couplant medium, located between said wedge means and said metal structure surface, for assuring efficient transmission of said Rayleigh wave into said wedge means;
   piezoelectric polymer transducer means, embedded within said wedge means and inclined at the critical angle for receiving said transmitted Rayleigh wave from said metal structure as a dilatation wave in said wedge means and converting said wave into a proportional electrical pulse, said transducer means being impedance matched to said wedge means;
   a plurality of conductors, attached to said transducer means and embedded within said wedge means, for receiving and transmitting said electrical pulse from said transducer means; and
   preamplifier means, attached to said plurality of conductors, for receiving and amplifying said electrical pulse.

17. An angle-beam transducer according to claim 16 wherein said plurality of conductors further comprise wires.

18. An angle-beam transducer according to claim 17 wherein said transducer means further comprises a thickness-mode piezoelectric polymer element.

19. An angle-beam transducer according to claim 18 wherein said wedge means is a plastic material having an impedance generally the same as said piezoelectric polymer element.

20. An angle-beam transducer according to claim 19 wherein said piezoelectric polymer is a polyvinylidene flouride.

21. An angle-beam transducer according to claim 20 wherein said plastic material is a polymethyl methacrylate.

22. An angle-beam transducer according to claim 21 wherein said wedge means further comprises a directional planar wedge having a preselected thickness and said polymer element further comprises a rectangular shaped element having a width corresponding to said wedge thickness.

23. An angle-beam transducer according to claim 21 wherein said wedge means further comprises a conical wedge having a preselected radius and said polymer element further comprises a corresponding conical element shaped such that an omnidirectional transducer is formed thereby.

24. An angle-beam transducer according to claim 20 wherein said plastic material is a polystyrene.

25. An angle-beam transducer according to claim 24 wherein said wedge means further comprises a directional planar wedge having a preselected thickness and said polymer element further comprises a rectangular shaped element having a width corresponding to said wedge thickness.

26. An angle-beam transducer according to claim 24 wherein said wedge means further comprises a conical wedge having a preselected radius and said polymer element further comprises a corresponding conical element shaped such that an omnidirectional transducer is formed thereby.

27. An angle-beam transducer according to claim 18 wherein said wedge means is a filled epoxy having an impedance generally the same as said piezoelectric polymer element.

28. An angle-beam transducer according to claim 27 wherein said piezoelectric polymer is a polyvinylidene flouride.

29. An angle-beam transducer according to claim 28 wherein said wedge means further comprises a directional planar wedge having a preselected thickness and said polymer element further comprises a rectangular shaped element having a width corresponding to said wedge thickness.

30. An angle-beam transducer according to claim 28 wherein said wedge means further comprises a conical wedge having a preselected radius and said polymer element further comprises a corresponding conical element shaped such that an omnidirectional transducer is formed thereby.

* * * * *